(12) United States Patent
Dantale et al.

(10) Patent No.: US 10,358,409 B2
(45) Date of Patent: *Jul. 23, 2019

(54) LOW-TOXICITY OLEFINIC ESTER COMPOSITIONS AND METHODS OF USING THE SAME

(71) Applicant: Elevance Renewable Sciences, Inc., Woodridge, IL (US)

(72) Inventors: Shubhada Dantale, Woodridge, IL (US); Frederyk Ngantung, Woodridge, IL (US); Selim Erhan, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/847,664

(22) Filed: Sep. 8, 2015

(65) Prior Publication Data

US 2016/0075631 A1  Mar. 17, 2016

Related U.S. Application Data

(60) Provisional application No. 62/050,630, filed on Sep. 15, 2014.

(51) Int. Cl.

| | | |
|---|---|---|
| *C07C 69/75* | (2006.01) | |
| *C07C 69/74* | (2006.01) | |
| *C07D 307/20* | (2006.01) | |
| *C07D 309/10* | (2006.01) | |
| *C07D 319/12* | (2006.01) | |
| *C07D 307/58* | (2006.01) | |
| *C07D 263/36* | (2006.01) | |
| *C07D 261/12* | (2006.01) | |
| *C07C 69/533* | (2006.01) | |

(52) U.S. Cl.
CPC ............ *C07C 69/75* (2013.01); *C07C 69/533* (2013.01); *C07C 69/74* (2013.01); *C07D 261/12* (2013.01); *C07D 263/36* (2013.01); *C07D 307/20* (2013.01); *C07D 307/58* (2013.01); *C07D 309/10* (2013.01); *C07D 319/12* (2013.01); C07C 2601/14 (2017.05)

(58) Field of Classification Search
CPC .................................. C07C 69/75; C07C 69/74
See application file for complete search history.

(56) References Cited

U.S. PATENT DOCUMENTS

| | | | | |
|---|---|---|---|---|
| 4,588,533 A | | 5/1986 | Berry, Jr. | |
| 8,557,864 B2* | | 10/2013 | Iinuma | A61K 31/20 514/17.7 |
| 9,045,447 B2* | | 6/2015 | Littich | C07C 51/347 |
| 2009/0131520 A1* | | 5/2009 | Yanagita | A61K 31/23 514/549 |
| 2010/0204498 A1* | | 8/2010 | Iinuma | A61K 31/20 554/121 |
| 2012/0264959 A1* | | 10/2012 | Iinuma | A61K 31/20 554/224 |
| 2013/0225470 A1* | | 8/2013 | Allen | C07C 233/09 510/382 |
| 2013/0296425 A1* | | 11/2013 | Iinuma | A61K 31/23 514/549 |
| 2013/0296426 A1* | | 11/2013 | Iinuma | A61K 31/23 514/552 |
| 2014/0275580 A1* | | 9/2014 | Littich | C07D 307/20 549/478 |
| 2016/0015684 A1* | | 1/2016 | Higuchi | A61K 31/381 514/289 |

FOREIGN PATENT DOCUMENTS

| WO | WO 2012105476 A1 * | 8/2012 | ............. A61K 31/23 |
|---|---|---|---|
| WO | WO 2012105477 A1 * | 8/2012 | ............. A61K 31/23 |

OTHER PUBLICATIONS

Neuhaus et al., Australian Chemical Institute Journal and Proceedings (1947), 14, pp. 286-289.*
Kuznetsov et al., Dopovidi Akedemii Nauk Ukrains'koi RSR, Seriya B: Geologiya, Geofizika, Khimiya to Biologiya (1969), 31(10), pp. 908-910.*
CAPLUS record of Seki et al. Phytochemistry 1994, 36, 425-31 (Year: 1994).*
STN Registry entry for Registry No. 151309-74-9, which entered STN on Nov. 18, 1993 (Year: 1993).*
STN Registry entry for Registry No. 874516-34-4, which entered STN on Feb. 17, 2006 (Year: 2006).*
STN Registry entry for Registry No. 103042-49-5, which entered STN on Jul. 4, 1986 (Year: 1986).*

(Continued)

*Primary Examiner* — Matthew P Coughlin
(74) *Attorney, Agent, or Firm* — Robert S. Dailey

(57) ABSTRACT

Compositions including certain olefinic ester compounds are generally disclosed. In some embodiments, such compositions are compositions having low toxicity, such as low aquatic toxicity. Therefore, in some embodiments, such compositions can be suitable used as solvents or as part of a solvent system for applications where low toxicity is desirable. Such uses include, but are not limited to, cleaning applications on or near waterways, use in oil or gas recovery, and the like. In some other embodiments, such compositions are treatment fluids for oil wells, and can therefore be introduced into an oil well to remove buildup and other deposits. In some embodiments, the olefinic ester compounds are derived from a natural oil or a natural oil derivative.

10 Claims, 1 Drawing Sheet

(56) References Cited

OTHER PUBLICATIONS

Ex parte Cao, Decision rendered by the Board of Patent Appeals and Interferences in U.S. Appl. No. 10/696,862 on Sep. 21, 2011 Year: 2011).*
CAS Registry Entry for Registry No. 1004521-26-9, which entered STN on Feb. 19, 2008 (Year: 2008).*
CAS Registry Entry for Registry No. 103330-87-6, which entered STN on Jul. 19, 1986 (Year: 1986).*
Haslbeck et al., Lipids, vol. 18(10), pp. 706-713 (1983).
Int'l Search Report & Written Opinion of the Int'l Searching Authority, PCT App. No. PCT/US2015/048896, dated Oct. 27, 2015.

* cited by examiner

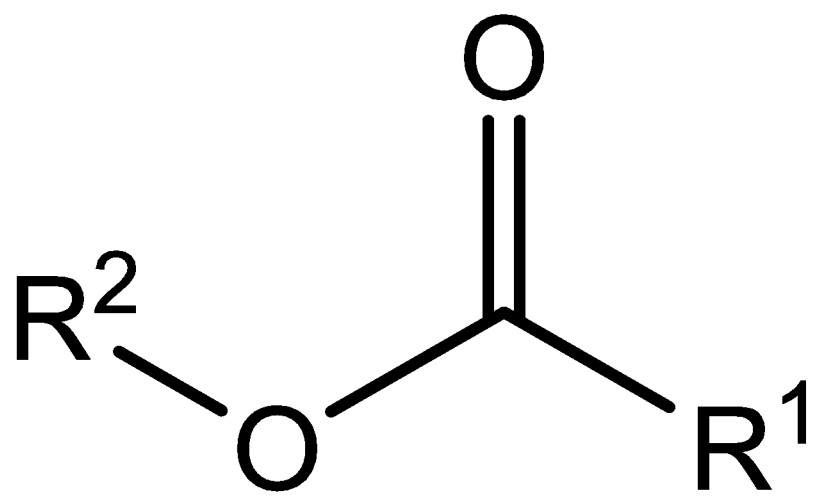

LOW-TOXICITY OLEFINIC ESTER COMPOSITIONS AND METHODS OF USING THE SAME

CROSS-REFERENCE TO RELATED APPLICATIONS

The present application claims the benefit of priority of U.S. Provisional Application No. 62/050,630, filed Sep. 15, 2014, which is hereby incorporated by reference in its entirety as though fully set forth herein.

TECHNICAL FIELD

Compositions including certain olefinic ester compounds are generally disclosed. In some embodiments, such compositions are compositions having low toxicity, such as low aquatic toxicity. Therefore, in some embodiments, such compositions can be suitable used as solvents or as part of a solvent system for applications where low toxicity is desirable. Such uses include, but are not limited to, cleaning applications on or near waterways, use in oil or gas recovery, and the like. In some other embodiments, such compositions are treatment fluids for oil wells, and can therefore be introduced into an oil well to remove buildup and other deposits. In some embodiments, the olefinic ester compounds are derived from a natural oil or a natural oil derivative.

BACKGROUND

The use of certain industrial solvents has curtailed in recent years due, in part, to concerns over their impact on the environment and their effects on general health and safety. This is especially true of solvents known to have a high volatile organic content (VOC), as such compounds may contribute to greenhouse gas production and ozone depletion. In some instances, traditional high VOC solvents can also be carcinogenic, teratogenic, toxic, and/or mutagenic. Therefore, a number of common solvents have come under increased regulatory scrutiny and therefore suffer from decreased use. Such solvents include aromatics (e.g., benzene, toluene, xylenes, and the like), ketones (e.g., methyl ethyl ketone, methyl isobutyl ketone, and the like), halogenated organics (e.g., dichloromethane, perchloroethylene, and the like), glycol ethers, and alcohols (e.g., methanol, isopropanol, ethylene glycol, and the like).

Certain derivatives of renewable feedstocks can provide more suitable alternatives to high VOC solvents. For example, fatty acid alkyl esters (e.g., from the transesterification of vegetable oils, animal fats, or other lipids) can provide environmentally friendly alternatives to traditional oxygenated solvents. Methyl soyate, for example, has a low VOC value, a high flash point, a low toxicity, and a high biodegradability. Terpene oils from citrus and pine (d-limonene and pinene, respectively) may also serve as suitable alternatives to certain traditional organic solvents.

Such renewable solvents are not without their problems, however. For example, d-limonene and dipentene (a racemate of d-limonene) are acute and chronic aquatic toxins, and also have an irritating and sensitizing effect on the skin. Further, d-limonene is highly inflammable (e.g., more so than petroleum distillates) and can be subject to fluctuations in supply and price. Fatty acid alkyl esters can overcome some of these deficiencies of terpene oils, but can also exhibit poor solvency relative to certain incumbents.

Thus, there is a continuing need to develop solvent compounds and compositions that are renewably sourced, exhibit high solvency, and have a desirable health and safety profile.

SUMMARY

In a first aspect, the disclosure provides compounds of formula (I):

wherein: $R^1$ is $C_{9-21}$ alkenyl, which is optionally substituted; $R^2$ is $R^3$ or $-G^3-R^3$; $G^3$ is $C_{1-6}$ alkylene or $C_{2-6}$ alkenylene, each of which is optionally substituted; and $R^3$ is $C_{3-20}$ cycloalkyl, $C_{2-20}$ heterocycloalkyl, $C_{6-20}$ aryl, or $C_{3-20}$ heteroaryl, each of which is optionally substituted. In some embodiments, the compound is cyclohexyl 9-dodecenoate. In some embodiments, such compounds are derived from a renewable source, such as a natural oil.

In a second aspect, the disclosure provides compositions including one or more compounds of the first aspect. In some embodiments, the composition comprises a carrier, such as an aqueous medium (e.g., water). In some embodiments, the composition is an oil-in-water emulsion. In some embodiments, the compositions are cleaning compositions. In some other embodiments, the compositions are fluids suitable for use in down-hole treatment of an oil well or a gas well. In some embodiments, such compositions can also be suitable for use in extracting carbonaceous material from bituminous sands (e.g., oil sands or tar sands).

In a third aspect, the disclosure provides methods for cleaning a surface, including: contacting a surface with one or more compounds of the first aspect or a composition of the second aspect. In some embodiments, the surface is a hard surface.

In a fourth aspect, the disclosure provides methods for treating an oil well, including: introducing into an oil well one or more compounds of the first aspect or a composition of the second aspect. In some embodiments, the treatment fluid is an aqueous composition, such as an oil-in-water emulsion.

In a fifth aspect, the disclosure provides methods for treating bituminous sand deposit, including: introducing to a bituminous sands deposit one or more compounds of the first aspect or a composition of the second aspect. In some embodiments, the treatment fluid is an aqueous composition, such as an oil-in-water emulsion.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

FIG. 1 shows an example of certain low-toxicity esters of the present disclosure, wherein $R^1$ is $C_{9-21}$ alkenyl, which is optionally substituted; $R^2$ is $R^3$ or -$G^3$-$R^3$; $G^3$ is $C_{1-6}$ alkylene or $C_{2-6}$ alkenylene, each of which is optionally substituted; and $R^3$ is $C_{3-20}$ cycloalkyl, $C_{2-20}$ heterocycloalkyl, $C_{6-20}$ aryl, or $C_{3-20}$ heteroaryl, each of which is optionally substituted.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms; and "$C_{x-y}$", which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2-14}$ range. Low-molecular-weight olefins include alpha-olefins, wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. Olefins in the $C_{4-10}$ range can also be referred to as "short-chain olefins," which can be either branched or unbranched. In one embodiments, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "acid," "acids," "carboxylic acid," or "carboxylic acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" or "carboxylic acids" may refer to a group of compounds with the general formula described above, wherein the compounds have different carbon lengths.

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. As used herein, the term "alkanol" refers to alcohols where R is an alkyl group.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. In some instances, the "alkyl" group can be divalent, in which case the group can alternatively be referred to as an "alkylene" group.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. In some instances, the "alkenyl" group can be divalent, in which case the group can alternatively be referred to as an "alkenylene" group.

As used herein, "halogen" or "halo" refers to a fluorine, chlorine, bromine, and/or iodine atom. In some embodiments, the terms refer to fluorine and/or chlorine.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Olefinic Ester Compounds

In certain aspects, the disclosure provides compounds of formula (I):

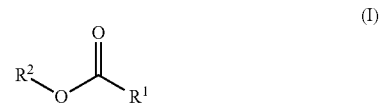

wherein: $R^1$ is $C_{9-21}$ alkenyl, which is optionally substituted; $R^2$ is $R^3$ or -$G^3$-$R^3$; $G^3$ is $C_{1-6}$ alkylene or $C_{2-6}$ alkenylene, each of which is optionally substituted; and $R^3$ is $C_{3-20}$ cycloalkyl, $C_{2-20}$ heterocycloalkyl, $C_{6-20}$ aryl, or $C_{3-20}$ heteroaryl, each of which is optionally substituted.

As noted above, $R^1$ is $C_{9-21}$ alkenyl, which is optionally substituted. The optional substituents can be any common substituents used in organic chemistry, including, but not limited to, halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, —$NH_2$ groups, —NH($C_{1-4}$ alkyl) groups, —N($C_{1-4}$ alkyl)$_2$ groups, —CN groups, —COOH groups, —COO($C_{1-4}$ alkyl) groups, —$CONH_2$ groups, —CONH($C_{1-4}$ alkyl) groups, —CON($C_{1-4}$ alkyl)$_2$ groups, —CHO groups, —CO($C_{1-4}$ alkyl) groups, or combinations thereof. In some embodiments, the optional substituents are selected from the group consisting of halogen atoms, $C_{1-4}$ alkoxy groups, $C_{1-4}$ fluoroalkoxy groups, —OH groups, and combinations thereof. In some embodiments, $R^1$ is $C_{11-15}$ alkenyl, which is optionally substituted according to the aforementioned embodiments. In some embodiments, $R^1$ is —$(CH_2)_7$—CH=$CH_2$. In some embodiments, $R^1$ is —$(CH_2)_7$—CH=CH—$CH_3$. In some embodiments, $R^1$ is —$(CH_2)_7$—CH=CH—$CH_2$—$CH_3$. In some embodiments, $R^1$ is —$(CH_2)_7$—CH=CH—$CH_2$—CH=$CH_2$, —$(CH_2)_7$—CH=CH—$CH_2$—$CH_2$—$CH_3$, or —$(CH_2)_{10}$—CH=$CH_2$. In some such embodiments, $R^1$ is —$(CH_2)_7$—CH=CH—$CH_2$—CH=$CH_2$. In some embodiments, $R^1$ is —$(CH_2)_7$—CH=CH—$CH_2$—CH=CH—$CH_3$, —$(CH_2)_7$—CH=CH—$CH_2$—$CH_2$—$CH_3$, or —$(CH_2)_{10}$—CH=CH—$CH_3$. In some such embodiments, $R^1$ is —$(CH_2)_7$—CH=CH—$CH_2$—CH=CH—$CH_3$. In some embodiments, $R^1$ is —$(CH_2)_7$—CH=CH—$CH_2$—CH=CH—$CH_2$—$CH_3$, —$(CH_2)_7$—CH=CH—$(CH_2)_4$—$CH_3$, or —$(CH_2)_{10}$—CH=CH—$CH_2$—$CH_3$. In some such embodiments, $R^1$ is —$(CH_2)_7$—CH=CH—$CH_2$—CH=CH—$CH_2$—$CH_3$.

In some embodiments of any of the above embodiments, $R^2$ is -$G^3$-$R^3$. In some embodiments, $R^2$ is $R^3$. In some other embodiments, $G^3$ is $C_{1-6}$ alkylene. In some embodiments, $G^3$ is —$CH_2$— or —$CH_2$—$CH_2$—. In some such embodiments, $G^3$ is —$CH_2$—. In some other embodiments, $G^3$ is —$CH_2$—$CH_2$—.

In some embodiments of any of the above embodiments, $R^3$ is $C_{3-20}$ cycloalkyl, which is optionally substituted. The optional substituents can be any common substituents used in organic chemistry, including, but not limited to, halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, —NH$_2$ groups, —NH($C_{1-4}$ alkyl) groups, —N($C_{1-4}$ alkyl)$_2$ groups, —CN groups, —COOH groups, —COO($C_{1-4}$ alkyl) groups, —CONH$_2$ groups, —CONH($C_{1-4}$ alkyl) groups, —CON($C_{1-4}$ alkyl)$_2$ groups, —CHO groups, —CO($C_{1-4}$ alkyl) groups, hydroxy- and/or $C_{1-4}$ alkoxy-substituted $C_{1-4}$ alkyl groups, or combinations thereof. In some embodiments, the optional substituents are selected from the group consisting of halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, hydroxy- and/or $C_{1-4}$ alkoxy-substituted $C_{1-4}$ alkyl groups and combinations thereof. In some embodiments, $R^3$ is $C_{3-12}$ cycloalkyl, which is optionally substituted according to any of the embodiments described above. In some embodiments, $R^3$ is cyclopropyl, cyclobutyl, cyclopentyl, cyclohexyl, cycloheptyl, cyclooctyl, norbornyl (e.g., norborn-1-yl), adamantyl (e.g., adamant-1-yl), cyclopropenyl, cyclobutenyl, cyclopentenyl, cyclohexenyl, cycloheptenyl, 1,3-cyclohexadienyl, 1,4-cyclohexadienyl, or 1,5-cyclooctadienyl. In some embodiments, $R^3$ is cyclopropyl, cyclobutyl, cyclopentyl, cyclohexyl, cycloheptyl, cyclooctyl, norbornyl (e.g., norborn-1-yl), or adamantyl (e.g., adamant-1-yl). In some embodiments, $R^3$ is cyclopentyl, cyclohexyl, norbornyl (e.g., norborn-1-yl), or adamantyl (e.g., adamant-1-yl). In some embodiments, $R^3$ is cyclopentyl or cyclohexyl. In some embodiments, $R^3$ is cyclohexyl.

In some embodiments of any of the above embodiments, $R^3$ is $C_{2-20}$ heterocycloalkyl, which is optionally substituted. The optional substituents can be any common substituents used in organic chemistry, including, but not limited to, halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, —NH$_2$ groups, —NH($C_{1-4}$ alkyl) groups, —N($C_{1-4}$ alkyl)$_2$ groups, —CN groups, —COOH groups, —COO($C_{1-4}$ alkyl) groups, —CONH$_2$ groups, —CONH($C_{1-4}$ alkyl) groups, —CON($C_{1-4}$ alkyl)$_2$ groups, —CHO groups, —CO($C_{1-4}$ alkyl) groups, hydroxy- and/or $C_{1-4}$ alkoxy-substituted $C_{1-4}$ alkyl groups, or combinations thereof. In some embodiments, the optional substituents are selected from the group consisting of halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, hydroxy- and/or $C_{1-4}$ alkoxy-substituted $C_{1-4}$ alkyl groups and combinations thereof. In some embodiments, $R^3$ is tetrahydrofuranyl, tetrahydropyranyl, or dioxanyl. In some embodiments, $R^3$ is tetrahydrofuranyl or tetrahydropyranyl.

In some embodiments of any of the above embodiments, $R^3$ is $C_{6-20}$ aryl, which is optionally substituted. The optional substituents can be any common substituents used in organic chemistry, including, but not limited to, halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, —NH$_2$ groups, —NH($C_{1-4}$ alkyl) groups, —N($C_{1-4}$ alkyl)$_2$ groups, —CN groups, —COOH groups, —COO($C_{1-4}$ alkyl) groups, —CONH$_2$ groups, —CONH($C_{1-4}$ alkyl) groups, —CON($C_{1-4}$ alkyl)$_2$ groups, —CHO groups, —CO($C_{1-4}$ alkyl) groups, hydroxy- and/or $C_{1-4}$ alkoxy-substituted $C_{1-4}$ alkyl groups, or combinations thereof. In some embodiments, the optional substituents are selected from the group consisting of halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, hydroxy- and/or $C_{1-4}$ alkoxy-substituted $C_{1-4}$ alkyl groups and combinations thereof. In some embodiments, $R^3$ is phenyl.

In some embodiments of any of the above embodiments, $R^3$ is $C_{3-20}$ heteroaryl, which is optionally substituted. The optional substituents can be any common substituents used in organic chemistry, including, but not limited to, halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, —NH$_2$ groups, —NH($C_{1-4}$ alkyl) groups, —N($C_{1-4}$ alkyl)$_2$ groups, —CN groups, —COOH groups, —COO($C_{1-4}$ alkyl) groups, —CONH$_2$ groups, —CONH($C_{1-4}$ alkyl) groups, —CON($C_{1-4}$ alkyl)$_2$ groups, —CHO groups, —CO($C_{1-4}$ alkyl) groups, hydroxy- and/or $C_{1-4}$ alkoxy-substituted $C_{1-4}$ alkyl groups, or combinations thereof. In some embodiments, the optional substituents are selected from the group consisting of halogen atoms, $C_{1-4}$ alkyl groups, $C_{1-4}$ fluoroalkyl groups, $C_{1-4}$ alkoxy groups, $C_{1-4}$ fluoroalkoxy groups, —OH groups, hydroxy- and/or $C_{1-4}$ alkoxy-substituted $C_{1-4}$ alkyl groups and combinations thereof. In some embodiments, $R^3$ is furanyl, oxazolyl, or isoxazolyl. In some embodiments, $R^3$ is furanyl.

In some embodiments, the compound of formula (I) is cyclohexyl 9-decenoate. In some other embodiments, the compound of formula (I) is cyclohexyl 9-dodecenoate.

Derivation from Renewable Sources

The olefinic ester compounds employed in any of the aspects or embodiments disclosed herein (e.g., compounds of formula (I)) can, in certain embodiments, be derived from renewable sources, such as from various natural oils and/or their derivatives. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the cross-metathesis reaction of the natural oil feedstock with a low-molecular-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA.

For example, the fatty acid portion of the esters disclosed herein can be derived from a natural oil by metathesis. For example, when esters of certain 18-carbon fatty acids having a carbon-carbon double bond in the 9-position (e.g., oleic acid, linoleic acid, linolenic acid, etc.) are cross-metathesized with 1-butene, the resulting product mixture can include certain esters of 9-decenoic acid and 9-dodenenoic acid. For fatty such fatty acids that also have a carbon-carbon double bond at the 12-position, the cross-metathesis of the fatty acid ester with 1-butene can give a product mixture that includes esters of 9,12-tridecadienoic acid and 9,12-pentadecadienoic acid. These esters can be treated through a transesterification (or a series of transesterifications) to obtain compounds such as those disclosed here. For example, in some embodiments, this transesterification (or series of transesterification reactions) can include reacting the fatty acid ester with cyclohexanol to yield cyclohexyl esters of 9-decenoic acid, 9-dodenenoic acid, 9,12-tridecadienoic acid, and 9,12-pentadecadienoic acid.

The conditions for such metathesis reactions, and the reactor design, and suitable catalysts are as described above with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than $-40°$ C., or greater than $-20°$ C., or greater than $0°$ C., or greater than $10°$ C. In certain embodiments, the metathesis reaction temperature is less than $200°$ C., or less than $150°$ C., or less than $120°$ C. In some embodiments, the metathesis reaction temperature is between $0°$ C. and $150°$ C., or is between $10°$ C. and $120°$ C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Compositions Including Olefinic Ester Compounds

In certain aspects, the disclosure provides compositions that include olefinic ester compounds, such as those disclosed above. Any suitable olefin ester compounds can be used in the compositions. In some embodiments, the olefinic ester compounds are compounds of formula (I), or any of the above embodiments thereof.

The composition can contain any suitable amount of the olefinic ester compounds. For example, in some embodiments, the olefinic ester compounds make up at least 1 percent by weight, or at least 3 percent by weight, or at least 5 percent by weight, or at least 10 percent by weight, or at least 15 percent by weight, or at least 20 percent by weight, of the composition, and up to 90 percent by weight, or up to 70 percent by weight, or up to 50 percent by weight. In some other embodiments, the olefinic ester compounds make up at least 30 percent by weight, or at least 40 percent by weight, or at least 50 percent by weight, or at least 60 percent by weight, or at least 70 percent by weight, or at least 75 percent by weight, of the composition, and up to 99 percent by weight, or up to 95 percent by weight, or up to 90 percent by weight.

The composition can contain one or more additional ingredients, in addition to the olefinic ester compounds. For example, in some embodiments, the composition further includes one or more of: a carrier, an additional solvent, a co-solvent, a surfactant, a co-surfactant, an emulsifier, a natural or synthetic colorant, a natural or synthetic fragrance, an antioxidant, a corrosion inhibitor, or an antimicrobial agent.

In some embodiments, the composition is an emulsion, such as a microemulsion. In some such embodiments, the composition further includes water and one or more emulsifiers. The type of emulsion can vary depending on the type of emulsion and the desired end uses. In some embodiments, for example, the composition is an oil-in-water emulsion, where there is a continuous aqueous phase with an oily phase dispersed in the aqueous phase. In some other embodiments, the composition is a water-in-oil emulsion, where there is a continuous oily phase with an aqueous phase dispersed in the oily phase.

In some embodiments, the compositions can include one or more additional ingredients or additives. Such additional ingredients or additives include, but are not limited to, carriers, solvents, co-solvents (such as longer-chain olefinic ester compounds), surfactants, co-surfactants, emulsifiers, natural or synthetic colorants, natural or synthetic fragrances, natural or synthetic deodorizers, antioxidants, corrosion inhibitors, chelating agents, precipitating and/or sequestering builders, and antimicrobial agents.

In embodiments that include surfactants, any suitable surfactants can be used. For example, in some embodiments, the surfactants used in the composition can include surfactants having an HLB (hydrophile-lipophile balance) of 4 to 14, or 8 to 13. In some embodiments, the surfactants used in the composition include the amine salts (e.g., the isopropyl amine salt) of dodecylbenzene sulfonic acid, the amine salts (e.g., the isopropyl amine salt) of oleic acid, linear alcohol alkoxylates, branched alcohol alkoxylates, alkyl phenol alkoxylates, fatty amides, fatty alkanolamides, fatty amine alkoxylates, sorbitan esters, glycerol esters, and combinations thereof. Other examples of suitable nonionic surfactants include, but are not limited to, linear alcohol alkoxylates, branched alcohol alkoxylates, alkyl phenol alkoxylates, fatty amides, fatty alkanolamides, fatty amine alkoxylates, and combinations thereof. Some other examples of suitable anionic surfactants include, but are not limited to, water-soluble salts of alkyl benzene sulfonates, alkyl sulfates, alkyl polyalkoxy ether sulfates, paraffin sulfonates, alpha-olefin sulfonates and sulfosuccinates, alpha-sulfocarboxylates and their esters, alkyl glyceryl ether sulfonates, fatty acid monoglyceride sulfates and sulfonates, alkyl phenol polyalkoxyether sulfates and combinations thereof. Other examples of suitable anionic surfactants include, but are not limited to, the water-soluble salts or esters of alpha-sulfonated fatty acids containing from about 6 to about 20 carbon atoms in the fatty acid group and from about 1 to about 10 carbon atoms in the ester group.

Such compositions may be useful in the preparation of emulsions (e.g., microemulsions or nanoemulsions), e.g., where the oily phase is emulsified in an aqueous medium. In such embodiments, the surfactants can include linear alcohol alkoxylates, branched alcohol alkoxylates, alkyl phenol alkoxylates, fatty amides, fatty alkanolamides, fatty amine alkoxylates and combinations thereof. In some such embodiments, the olefinic ester compound if the primary solvent.

In certain aspects and embodiments, such compositions can be used in a cleaning method, where the cleaning composition is applied to a surface (e.g., a surface to be cleaned). In some such embodiments, the surface can be washed with an aqueous medium (e.g., water) after application of the cleaning composition. In some other embodiments, the compositions can be used in certain down-the-hole oilfield applications, such as breaking up asphaltenes and other materials in an oil or gas well, or in a bituminous sands deposit.

In some embodiments, nonionic surfactants having an HLB of from about 4 to about 14, or from 8 to 13, may be suitable in the preparation of a microemulsion. Non-limiting examples of such surfactants include, but are not limited to, linear alcohol alkoxylates, branched alcohol alkoxylates, alkyl phenol alkoxylates, fatty amides, fatty amide alkoxylates, fatty amine alkoxylates and combinations thereof.

In some embodiments, cationic surfactants can be used. Suitable cationic surfactants include, but are not limited to, water-soluble quaternary ammonium salts fatty amines, ammonium salts of fatty amines, quaternary ammonium salts of ethoxylated fatty amines, ammonium salts of ethoxylated fatty amines, quaternary ammonium salts of modified alkyl polyglucosides, and combinations thereof.

In some embodiments, the cleaning composition (e.g., a microemulsion) can include a nonionic and/or amphoteric surfactant. In some such embodiments, the olefinic ester compound is a primary solvent.

In some embodiments, nonionic surfactants and/or amphoteric surfactants can be used, e.g., nonionic surfactants having an HLB of from 4 to 14, or 8 to 13, e.g., in a microemulsion. Non-limiting examples of nonionic surfactants include, but are not limited to, linear alcohol alkoxylates, branched alcohol alkoxylates, alkyl phenol alkoxylates, fatty amides, fatty amide alkoxylates, fatty amine alkoxylates and combinations thereof. Non-limiting examples of amphoteric surfactants include, but are not limited to, water-soluble $C_{6-12}$ fatty amidoamine betaines, $C_{6-12}$ fatty amidoamine sultaines and hydroxysultaines, $C_{6-12}$ fatty amidoamine oxides, fatty iminodiproponiates, $C_{6-12}$ fatty amine betaines, $C_{6-12}$ fatty amines sultaines, $C_{6-12}$ fatty amine hydroxysultaines, $C_{6-12}$ fatty amine oxides, and combinations thereof.

In some embodiments, other surfactants can be used, either in combination with one or more of anionic, cationic and/or amphoteric surfactants (e.g., as short-chain co-surfactants) or alone. Non-limiting examples of such other surfactants include, but are not limited to, $C_{3-6}$ alcohols, glycols, glycol ethers, pyrrolidones, glycol ether esters, and combinations thereof.

In some embodiments, the composition comprises water. In some such embodiments, the composition is an emulsion, meaning that the composition includes two or more phases where at least one of the phases is at least partially dispersed in one or more of the other phases. In some further such embodiments, the composition is a microemulsion or a nanoemulsion, meaning that at least one of the phases is dispersed as small droplets whose size is on the order of about 1 nm up to about 1 micron. In some embodiments, the droplet size is less than the wavelength of the lowest energy visible light, e.g., less than 350 nm, or less than 300 nm, or less than 250 nm, or less than 200 nm, or less than 150 nm, or less than 100 nm, down to about 50 nm.

In some other embodiments, the composition is substantially free of water. For example, in some embodiments, the composition includes less than 2 percent by weight, or less than 1 percent by weight, or less than 0.5 percent by weight, or less than 0.1 percent by weight water, based on the total weight of the composition.

In some embodiments, the composition also includes alkanol esters (e.g., methyl esters) of saturated carboxylic acids, referred to herein as "saturated ester compounds."

The composition can contain any suitable distribution of olefinic ester compounds. For example, in some embodiments, the composition includes at least 50 percent by weight, or at least 60 percent by weight, or at least 70 percent by weight, or at least 80 percent by weight cycloalkyl or cycloalkyl-containing esters (e.g., cyclohexyl esters) of $C_{12}$ carboxylic acids having one or more carbon-carbon double bonds, based on the total weight of olefinic ester compounds and saturated ester compounds in the composition. In some embodiments, said $C_{12}$ carboxylic acids have one carbon-carbon double bond. In some embodiments, the composition includes at least 50 percent by weight, or at least 60 percent by weight, or at least 70 percent by weight, or at least 75 percent by weight of cyclohexyl esters of 9-decenoic acid, 9-undecenoic acid, or 9-dodecenoic acid, based on the total weight of olefinic ester compounds and saturated ester compounds in the composition. In some embodiments, the composition includes at least 50 percent by weight, or at least 60 percent by weight, or at least 70 percent by weight, or at least 75 percent by weight of cyclohexyl esters of 9-dodecenoic acid, based on the total weight of olefinic ester compounds and saturated ester compounds in the composition. In some such embodiments, the composition includes no more than 20 percent by weight, or no more than 15 percent by weight, or no more than 10 percent by weight of saturated ester compounds, based on the total weight of olefinic ester compounds and saturated ester compounds.

In some other embodiments, the composition includes at least 40 percent by weight, or at least 50 percent by weight, or at least 60 percent by weight, or at least 70 percent by weight, or at least 80 percent by weight, or at least 90 percent by weight, or at least 95 percent by weight, of $C_{12}$ olefinic ester compounds (e.g., cycloalkyl esters of 9-dodecenoic acid), based on the total weight of the composition or the total weight of the oily phase of an oil-in-water emulsion (excluding emulsifiers) or a water-in-oil emulsion (excluding emulsifiers). In some such embodiments, the composition includes 50 to 99 percent by weight, or 60 to 99 percent by weight, of $C_{12}$ olefinic ester compounds (e.g., cycloalkyl esters of 9-dodecenoic acid), based on the total weight of the composition or the total weight of the oily phase of an oil-in-water emulsion (excluding emulsifiers) or a water-in-oil emulsion (excluding emulsifiers)

In some such embodiments, the composition can also include various amounts of $C_{13-15}$ olefinic ester compounds, e.g., cycloalkyl esters of 9,12-tridecadienoic acid, cycloalkyl esters of 9,12-pentadecadienoic acid, and the like. In some embodiments, the composition includes up to 30 percent by weight, or up to 25 percent by weight, or up to 20 percent by weight, or up to 15 percent by weight, or up to 10 percent by weight, $C_{13}$ olefinic ester compounds (e.g., cycloalkyl esters of 9,12-tridecanedienoic acid), based on the total weight of the composition or the total weight of the oily phase of an oil-in-water emulsion (excluding emulsifiers) or water-in-oil emulsions (excluding emulsifiers). In some embodiments, the composition includes up to 35 percent by weight, or up to 30 percent by weight, or up to 25 percent by weight, or up to 20 percent by weight, or up to 15 percent by weight, $C_{15}$ olefinic ester compounds (e.g., cycloalkyl esters of 9,12-pentadecanedienoic acid), based on the total weight of the composition or the total weight of the oily phase of an oil-in-water emulsion (excluding emulsifiers) or water-in-oil emulsions (excluding emulsifiers)

In some such embodiments, the composition can also include an amount of olefin, e.g., alkenes. In some embodiments, the composition includes from 1 to 10 percent by weight, or from 1 to 7 percent by weight, alkenes, based on the total weight of the composition or the total weight of the oily phase of an oil-in-water emulsion (excluding emulsifiers). In some embodiments, the composition includes from 2 to 10 percent by weight, or from 2 to 7 percent by weight, alkenes, based on the total weight of the composition or the total weight of the oily phase of an oil-in-water emulsion (excluding emulsifiers). In some embodiments, the composition includes from 3 to 10 percent by weight, or from 3 to 7 percent by weight, alkenes, based on the total weight of the composition or the total weight of the oily phase of an oil-in-water emulsion (excluding emulsifiers).

In some embodiments, the compositions include an amount of certain oligomerized or polymerized fatty acid esters, such as POLARTECH LA 8005 (Afton Chemical Corp., Richmond, Va.) or other like compounds. Such compounds can be used in any suitable amount, such as up to 5 percent by weight, or up to 10 percent by weight, or up to 15 percent by weight, or up to 20 percent by weight, based on the total weight of oily components (e.g., fatty acid esters) in the composition.

In some embodiments, the composition includes certain low-molecular-weight (<200 amu) ketones. In some embodiments, the ketones are cyclic ketones, such as cyclohexanone. Such compounds can be used in any suitable amount, such as up to 5 percent by weight, or up to 10 percent by weight, or up to 15 percent by weight, or up to 20 percent by weight, or up to 25 percent by weight, based on the total weight of oily components in the composition.

Cleaning Compositions and Methods of Use

In certain aspects, the disclosed compositions are cleaning compositions and can therefore be used for cleaning. In some embodiments, the disclosure provides methods for cleaning a surface, such as a hard surface, including contacting a surface (e.g., with an effective amount, or a cleaning-effective amount) with a composition according to any of the above embodiments.

The cleaning capability of the compositions is not limited to any particular type of surface, including both hard and porous surfaces). The compositions can be used effectively on a variety of surfaces, including, but not limited to, plastics, other polymeric materials, metals, wood, glass, ceramic, rock (e.g., granite, marble, etc.), and various synthetic countertop materials. Further, the compositions may be used effectively to remove a variety of different materials from the surface. Such materials to be removed include, but are not limited to, chewing gum, paint (e.g., graffiti), grease (including lithium-based and molybdenum-based greases), oil, ink, fine particulate matter (e.g., coal dust), and any combinations thereof.

In some embodiments, an effective amount or a cleaning-effective amount of the composition is used. This amount can be determined readily based on the particular application, based on factors such as the nature of the surface, the nature of the material to be removed, the amount of the material to be removed, and the like.

Compositions for Treating Oil Wells

In certain aspects, the disclosed compositions are compositions useful for treating oil wells, e.g., as part of the drilling process. Thus, in some embodiments, the disclosure provides methods for treating a well (e.g., an oil well), including introducing to the well (e.g., an effective amount) a composition according to any of the above embodiments. In some embodiments, the well is an oil well or a bituminous sands deposit.

The treatment composition can be introduced into the well in any suitable manner and at any suitable time. For example, in some embodiments, the treatment composition is introduced during the drilling process, e.g., by production tuning or other similar mechanisms. In other embodiments, the treatment composition is introduced after certain drilling operations, for example, for purposes of well remediation. The treatment fluid can be used to improve the effectiveness of the drilling process, for example, by removing drilling fluid muds, dispersing fine particles (fines), paraffins, asphaltenes, and other deposits in the well. In some embodiments, the methods disclosed herein employ an effective amount of the treatment fluid. The determination of an effective amount will depend on the circumstances surrounding the composition's use, and may depend on factors including, but not limited to, the nature of the well, the geologic composition of the well site, the method of drilling, and the other materials used in the drilling process.

EXAMPLES

Example 1

Sample Preparation

Six compositions were prepared. Composition 1A included 90 wt % cyclohexyl 9-decenoate in a mixture with POLARTECH LA 8005 (Afton Chemical Co., Richmond, Va.) (10 wt %). Composition 1B included 90 wt % cyclohexyl 9-dodecenoate in a mixture with POLARTECH LA 8005 (10 wt %). Composition 1C included a mixture of $C_{12-16}$ cyclohexyl esters (32 wt % 9,12-tridecadienoate, 29 wt % myristate, 12% palmitate, 7 wt % 9-dodecenoate, 6% 9,12-pentadecadienoate, 6% 9-pentadecenoate, 8% other unsaturated $C_{12-16}$ esters) at 90 wt % in a mixture with POLARTECH LA 8005 (10 wt %). Composition 1D included 61 wt % cyclohexyl 9-decenoate in a mixture with POLARTECH LA 8005 (9 wt %), ACTRASOL MY-75 (Afton Chemical Co., Richmond, Va.) (17 wt %), and cyclohexanone (13 wt %). Composition 1E included 61 wt % cyclohexyl 9-dodecenoate in a mixture with POLARTECH LA 8005 (9 wt %), ACTRASOL MY-75 (17 wt %), and cyclohexanone (13 wt %). Composition 1F included a mixture of $C_{12-16}$ cyclohexyl esters (32 wt % 9,12-tridecadienoate, 29 wt % myristate, 12% palmitate, 7 wt % 9-dodecenoate, 6% 9,12-pentadecadienoate, 6% 9-pentadecenoate, 8% other unsaturated $C_{12-16}$ esters) in a mixture with POLARTECH LA 8005 (9 wt %), ACTRASOL MY-75 (17 wt %), and cyclohexanone (13 wt %).

Example 2

Aquatic Toxicity

The aquatic toxicity of three cyclohexyl esters were tested against three comparative compounds. Aqueous samples of the following solvents were prepared at concentrations of 3200 mg/kg: xylene (Sample 2A); methyl 9-dodecenoate (Sample 2B); methyl esters of a mixture of $C_{13-15}$ olefinic acids (Sample 2C); cyclohexyl 9-decenoate (Sample 2D); cyclohexyl 9-dodecenoate (Sample 2E); and cyclohexyl esters of a mixture of $C_{13-15}$ olefinic acids. Using United States Environmental Protection Agency (EPA) Test No. 1644, the toxicity of the aqueous compositions was measured as the percent survival of *leptocheirus plumolosus* after 10 days of exposure. Table 1 recites the survival rates for each of the above compositions.

TABLE 1

| Sample | Survival Rate (%) |
|--------|-------------------|
| 2A | 69 |
| 2B | 47 |
| 2C | 52 |
| 2D | 57 |
| 2E | 89 |
| 2F | 91 |

What is claimed is:
1. A compound of formula (I):

wherein:
  $R^1$ is —(CH$_2$)$_7$—CH=CH—CH$_2$—CH$_3$;
  $R^2$ is $R^3$ or -$G^3$-$R^3$;
  $G^3$ is —CH$_2$— or —CH$_2$—CH$_2$—; and
  $R^3$ is:
    $C_{3-12}$ cycloalkyl, which is optionally substituted with one or more substituents selected from the group consisting of halogen atoms, unsubstituted $C_{1-4}$ alkyl groups, $C_{1-4}$ fluoroalkyl groups, $C_{1-4}$ alkoxy groups, $C_{1-4}$ fluoroalkoxy groups, —OH groups, —NH$_2$ groups, —NH(C$_{1-4}$ alkyl) groups, —N(unsubstituted $C_{1-4}$ alkyl)$_2$ groups, —CN groups, —COOH groups, —COO(C$_{1-4}$ alkyl) groups, —CONH$_2$ groups, —CONH(C$_{1-4}$ alkyl) groups, —CON(C$_{1-4}$ alkyl)$_2$ groups, —CHO groups, —CO(C$_{1-4}$ alkyl) groups, hydroxy- and/or C$_{1-4}$ alkoxy-substituted C$_{1-4}$ alkyl groups, and any combinations thereof;

C$_{2-20}$ heterocycloalkyl, which is optionally substituted with one or more substituents selected from the group consisting of halogen atoms, unsubstituted C$_{1-4}$ alkyl groups, C$_{1-4}$ fluoroalkyl groups, C$_{1-4}$ alkoxy groups, C$_{1-4}$ fluoroalkoxy groups, —OH groups, —NH$_2$ groups, —NH(C$_{1-4}$ alkyl) groups, —N(C$_{1-4}$ alkyl)$_2$ groups, —CN groups, —COOH groups, —COO(C$_{1-4}$ alkyl) groups, —CONH$_2$ groups, —CONH(C$_{1-4}$ alkyl) groups, —CON(C$_{1-4}$ alkyl)$_2$ groups, —CHO groups, —CO(C$_{1-4}$ alkyl) groups, hydroxy- and/or C$_{1-4}$ alkoxy-substituted C$_{1-4}$ alkyl groups, and any combinations thereof;

C$_{6-20}$ aryl, which is optionally substituted with one or more substituents selected from the group consisting of halogen atoms, unsubstituted C$_{1-4}$ alkyl groups, C$_{1-4}$ fluoroalkyl groups, C$_{1-4}$ alkoxy groups, C$_{1-4}$ fluoroalkoxy groups, —OH groups, —NH$_2$ groups, —NH(C$_{1-4}$ alkyl) groups, —N(unsubstituted C$_{1-4}$ alkyl)$_2$ groups, —CN groups, —COOH groups, —COO(C$_{1-4}$ alkyl) groups, —CONH$_2$ groups, —CONH(C$_{1-4}$ alkyl) groups, —CON(C$_{1-4}$ alkyl)$_2$ groups, —CHO groups, —CO(C$_{1-4}$ alkyl) groups, hydroxy- and/or C$_{1-4}$ alkoxy-substituted C$_{1-4}$ alkyl groups, and any combinations thereof; or C$_{3-20}$ heteroaryl, which is optionally substituted.

2. The compound of claim 1, wherein R$^2$ is -G$^3$-R$^3$.

3. The compound of claim 1, wherein R$^2$ is R$^3$.

4. The compound of claim 3, wherein R$^3$ is C$_{3-12}$ cycloalkyl, which is optionally substituted with one or more substituents selected from the group consisting of halogen atoms, unsubstituted C$_{1-4}$alkyl groups, C$_{1-4}$fluoroalkyl groups, C$_{1-4}$alkoxy groups, C$_{1-4}$ fluoroalkoxy groups, —OH groups, —NH$_2$ groups, —NH(C$_{1-4}$ alkyl) groups, —N(unsubstituted C$_{1-4}$ alkyl)$_2$ groups, —CN groups, —COOH groups, —COO(C$_{1-4}$ alkyl) groups, —CONH$_2$ groups, —CONH(C$_{1-4}$ alkyl) groups, —CON(C$_{1-4}$ alkyl)$_2$ groups, —CHO groups, —CO(C$_{1-4}$alkyl) groups, hydroxy- and/or C$_{1-4}$alkoxy-substituted C$_{1-4}$alkyl groups, and any combinations thereof.

5. The compound of claim 4, wherein R$^3$ is cyclopentyl, cyclohexyl, norbornyl, or adamantyl.

6. The compound of claim 5, wherein R$^3$ is cyclohexyl.

7. The compound of claim 3, where R$^3$ is C$_{2-2C}$ heterocycloalkyl, which is optionally substituted with one or more substituents selected from the group consisting of halogen atoms, unsubstituted C$_{1-4}$ alkyl groups, C$_{1-4}$ fluoroalkyl groups, C$_{1-4}$ alkoxy groups, C$_{1-4}$ fluoroalkoxy groups, —OH groups, —NH$_2$ groups, —NH(C$_{1-4}$ alkyl) groups, —N(C$_{1-4}$ alkyl)$_2$ groups, —CN groups, —COOH groups, —COO(C$_{1-4}$ alkyl) groups, —CONH$_2$ groups, —CONH(C$_{1-4}$ alkyl) groups, —CON(C$_{1-4}$ alkyl)$_2$ groups, —CHO groups, —CO(C$_{1-4}$ alkyl) groups, hydroxy- and/or C$_{1-4}$ alkoxy-substituted C$_{1-4}$ alkyl groups, and any combinations thereof.

8. The compound of claim 7, wherein R$^3$ is tetrahydrofuranyl, tetrahydropyranyl, or dioxanyl.

9. The compound of claim 3, wherein R$^3$ is phenyl.

10. The compound of claim 3, wherein R$^3$ is furanyl, oxazolyl, or isoxazolyl.

* * * * *